(12) United States Patent
Crass

(10) Patent No.: US 9,014,331 B2
(45) Date of Patent: Apr. 21, 2015

(54) RADIATION PROTECTION CURTAIN

(71) Applicant: Smiths Heimann GmbH, Wiesbaden (DE)

(72) Inventor: Matthias Crass, Griesheim (DE)

(73) Assignee: Smiths Heimann GmbH, Wiesbaden (DE)

( * ) Notice: Subject to any disclaimer, the term of this patent is extended or adjusted under 35 U.S.C. 154(b) by 109 days.

(21) Appl. No.: 13/732,653

(22) Filed: Jan. 2, 2013

(65) Prior Publication Data

US 2013/0114788 A1 May 9, 2013

Related U.S. Application Data

(63) Continuation of application No. PCT/EP2011/002584, filed on May 24, 2011.

(30) Foreign Application Priority Data

Jul. 1, 2010 (DE) .......................... 10 2010 025 831

(51) Int. Cl.
*G21F 3/00* (2006.01)
*G21F 1/10* (2006.01)
*G01N 23/04* (2006.01)

(52) U.S. Cl.
CPC .. *G21F 3/00* (2013.01); *G21F 1/10* (2013.01); *G01N 23/04* (2013.01)

(58) Field of Classification Search
CPC ........................................................ G21F 3/00
USPC .................................................... 378/57, 203
See application file for complete search history.

(56) References Cited

U.S. PATENT DOCUMENTS

| | | | | |
|---|---|---|---|---|
| 3,967,129 | A * | 6/1976 | Winkler | ..................... 250/517.1 |
| 4,020,346 | A | 4/1977 | Dennis | |
| 4,736,608 | A * | 4/1988 | Laws et al. | ...................... 72/200 |
| 5,870,449 | A | 2/1999 | Lee et al. | |
| 2003/0002630 | A1 | 1/2003 | Doenges | |
| 2004/0016271 | A1 | 1/2004 | Shah et al. | |
| 2008/0025470 | A1 * | 1/2008 | Streyl | ............................ 378/203 |

FOREIGN PATENT DOCUMENTS

| | | |
|---|---|---|
| DE | 43 01 908 A1 | 8/1994 |
| EP | 0 011 338 A1 | 5/1980 |
| EP | 0 393 214 A1 | 10/1990 |
| EP | 1 271 556 A1 | 1/2003 |
| EP | 2 194 373 A1 | 6/2010 |
| GB | 1 603 654 | 11/1981 |

* cited by examiner

*Primary Examiner* — Hoon Song
(74) *Attorney, Agent, or Firm* — Muncy, Geissler, Olds & Lowe, P.C.

(57) ABSTRACT

A radiation tunnel of an X-ray test device is shielded in by means of a radiation protection curtain in order that no impermissible radiation emerges. The radiation protection curtain is constructed from plates which are connected to one another in a manner of a downwardly suspended flat-top chain and are produced from a plastics composite that absorbs X-rays.

10 Claims, 5 Drawing Sheets

RADIATION PROTECTION CURTAIN

This nonprovisional application is a continuation of International Application No. PCT/EP2011/002584, which was filed on May 24, 2011, and which claims priority to German Patent Application No. 10 2010 025 831.8, which was filed in Germany on Jul. 1, 2010, and which are both herein incorporated by reference.

BACKGROUND OF THE INVENTION

1. Field of the Invention

The present invention relates to a radiation protection curtain and an x-ray inspection device, equipped with the radiation protection curtain.

2. Description of the Background Art

As is known, x-ray inspection systems, which have a radiation tunnel having at least one radiation source arranged therein, are employed for inspecting objects such as items of luggage for suspicious articles. To irradiate the objects, these are transported by a conveying device through the radiation tunnel, which must be shielded outwardly in such a way that no impermissible radiation emerges.

For the purpose of shielding the radiation tunnel, EP 1 271 556 A1, which corresponds to U.S. Pat. No. 6,663,280, and which is incorporated herein by reference, discloses closing the entrance and exit of the tunnel by means of radiation protection curtains made of lead. Lead curtains have the disadvantage that they can be moved to the side by the inspection object being transported in and out and thus no longer cover the entire opening.

Further, the great weight of conventional lead curtains and the great friction can have the result that especially light objects are overturned or even remain hanging on the curtain.

SUMMARY OF THE INVENTION

It is therefore an object of the invention to provide a radiation protection curtain, which securely shields a radiation tunnel outwardly and at the same time does not have the above-described disadvantages.

This object is attained in an embodiment in that the radiation protection curtain is constructed of plates, which are connectable together in the manner of a downwardly hanging flat-top chain and are made of an x-ray-absorbing plastic composite.

The structure of the curtain has the further advantage that it can be constructed of individual, flat-top chains, hanging downwardly next to one another, with a narrow width. An item of luggage transported through the curtain therefore presses back only the area of the curtain corresponding to the luggage width. Likewise, the individual plates, forming the chain links, can be configured in their height so that a chain is formed from at least 5, preferably from more than 10 links. Thus, during passage of an item of luggage, the opening of the curtain also adjusts to the height of the item of luggage. Openings in the curtain through which radiation can escape to the outside are thereby greatly minimized.

The production of the plates from an x-ray-absorbing plastic composite makes it possible to reduce the friction compared with lead curtains, because the plates can be provided with a smooth surface. Moreover, injection-moldable plastic composite materials can be used. Thus, complicated shapes, for example, plates with complex hinged parts, can also be produced. Plastic composite materials of this type with x-ray-absorbing properties can be obtained on the market.

An x-ray inspection device for examining objects, particularly items of luggage, with the use of x-rays comprises, apart from a radiation tunnel in which at least one radiation source is arranged, a conveying device for the objects, which runs through the radiation tunnel. At least the entrance, preferably the exit of the radiation tunnel as well, is shielded outwardly with a radiation protection curtain according to the invention. The radiation protection curtain therefore closes the opening area of the tunnel above the conveying device and during the entry or exiting of an item of luggage is partially lifted by said item.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figures 1, 2:
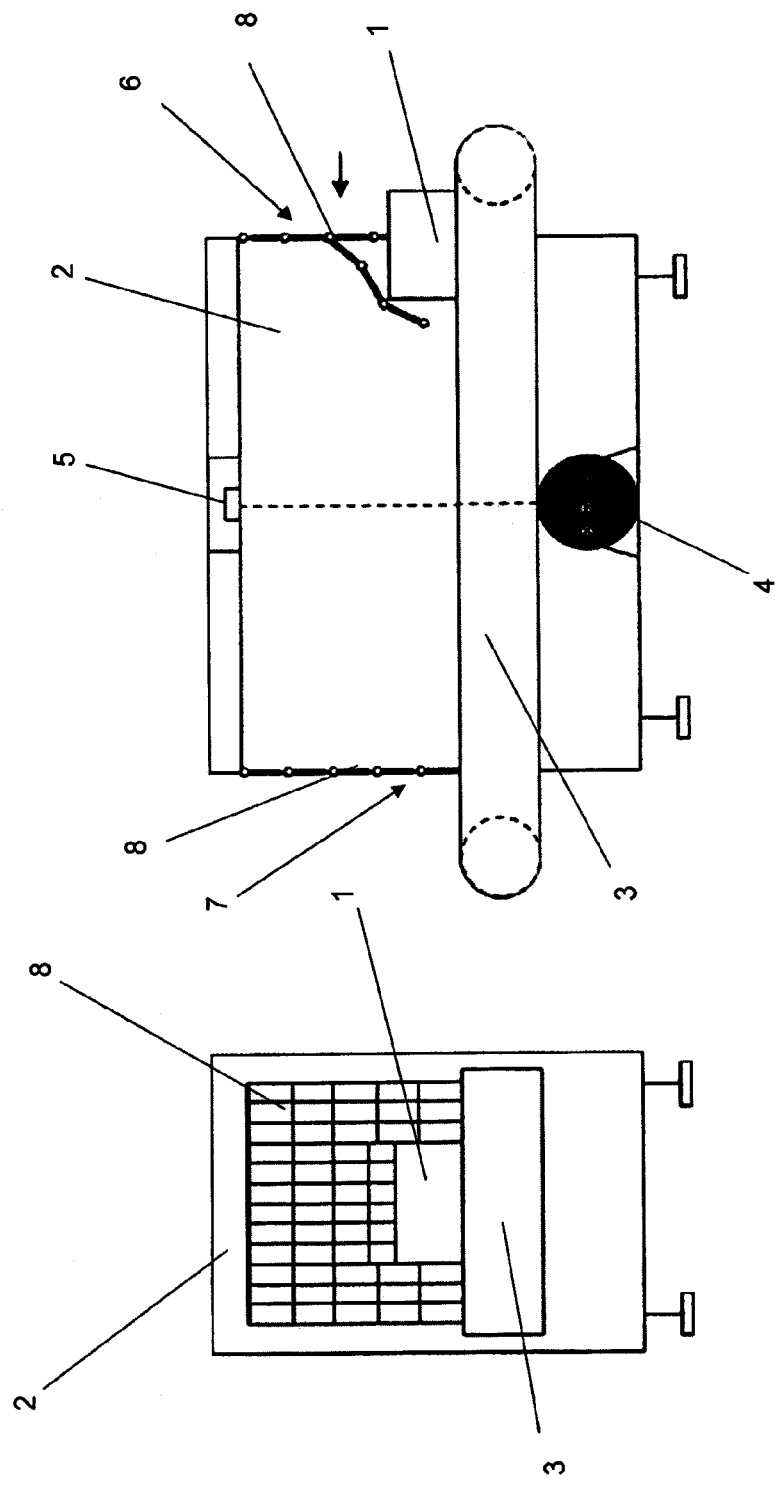
FIG. 1 and FIG. 2 show schematically an x-ray inspection device in a side and front view.
Figure 3:
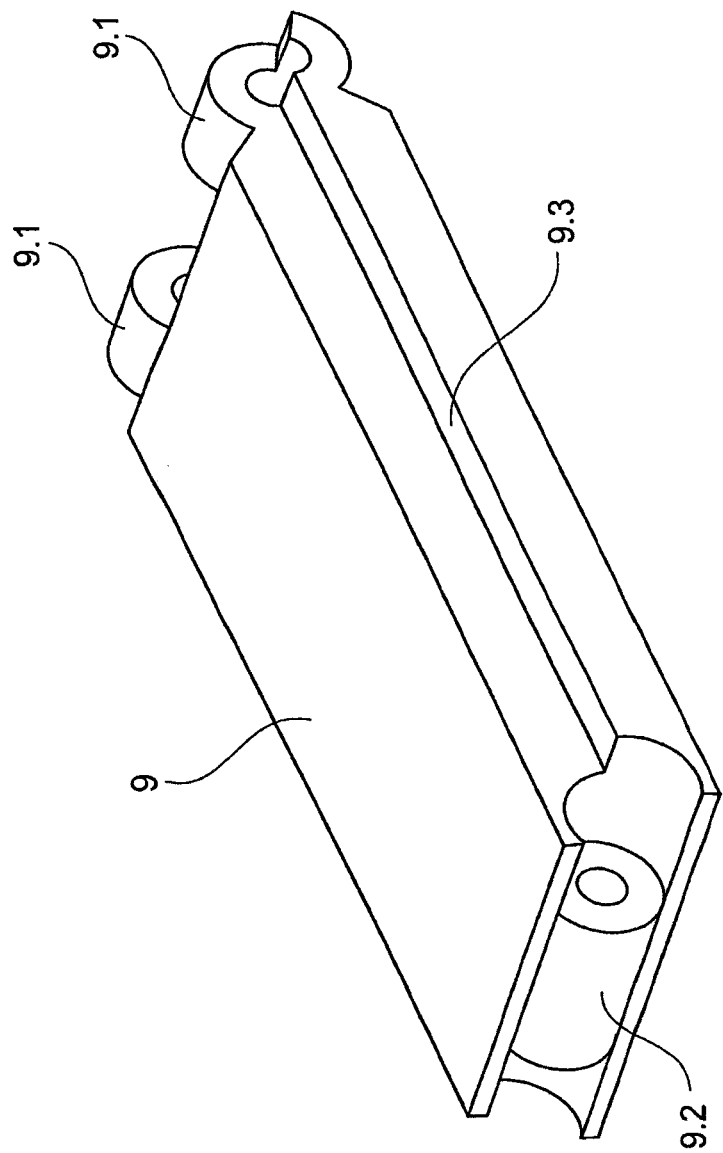
FIG. 3 shows in an oblique view a plate of the radiation protection curtain, which is configured as a link of a flat-top chain.
Figure 4:
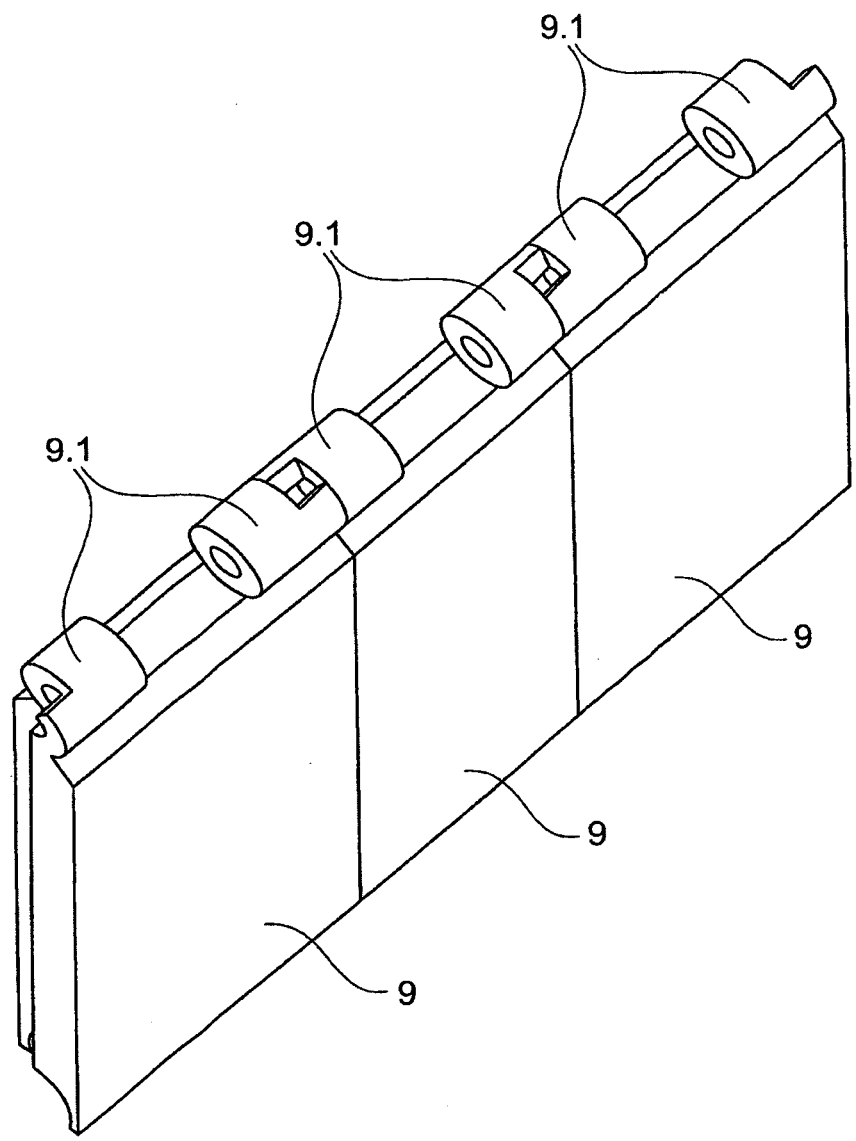
FIG. 4 shows in an oblique view three plates, arranged overlapping next to one another, of three vertical links.
Figure 5:
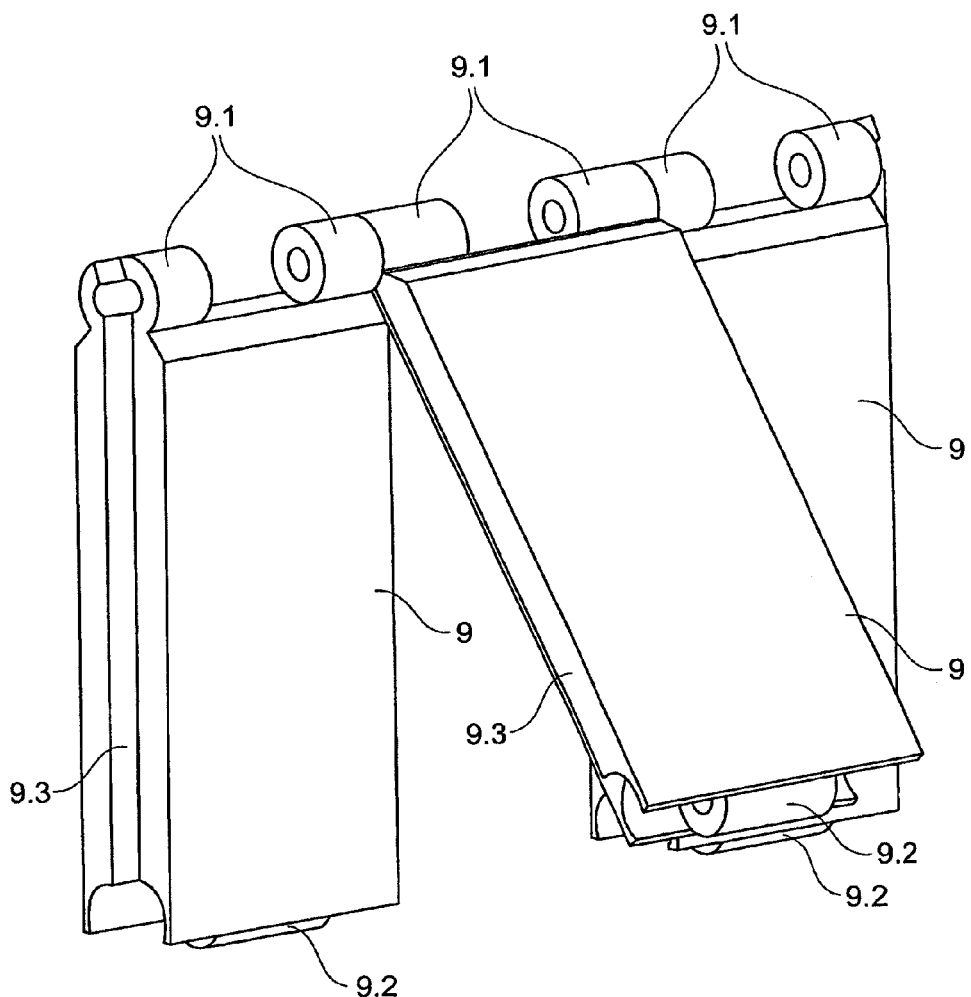
FIG. 5 shows the middle plate of FIG. 4 in a lifted-up position.

An x-ray inspection device which is used for examining objects 1 for suspicious articles is shown schematically in FIGS. 1 and 2. The preferred field of application is the inspection of luggage carried by passengers, however, packages, parcels, cargo, shipping containers, and other items can be examined by the device of the present invention.

The inspection device contains a radiation tunnel 2, through which a belt conveyor 3 runs as a conveying device. Objects 1 are guided through radiation tunnel 2 on belt conveyor 3. A radiation source 4 for x-raying objects 1 is arranged in the radiation tunnel. A detector array 5, by which rays not absorbed by object 1 are detected for an evaluation, is oriented toward radiation source 4.

Figure 6:
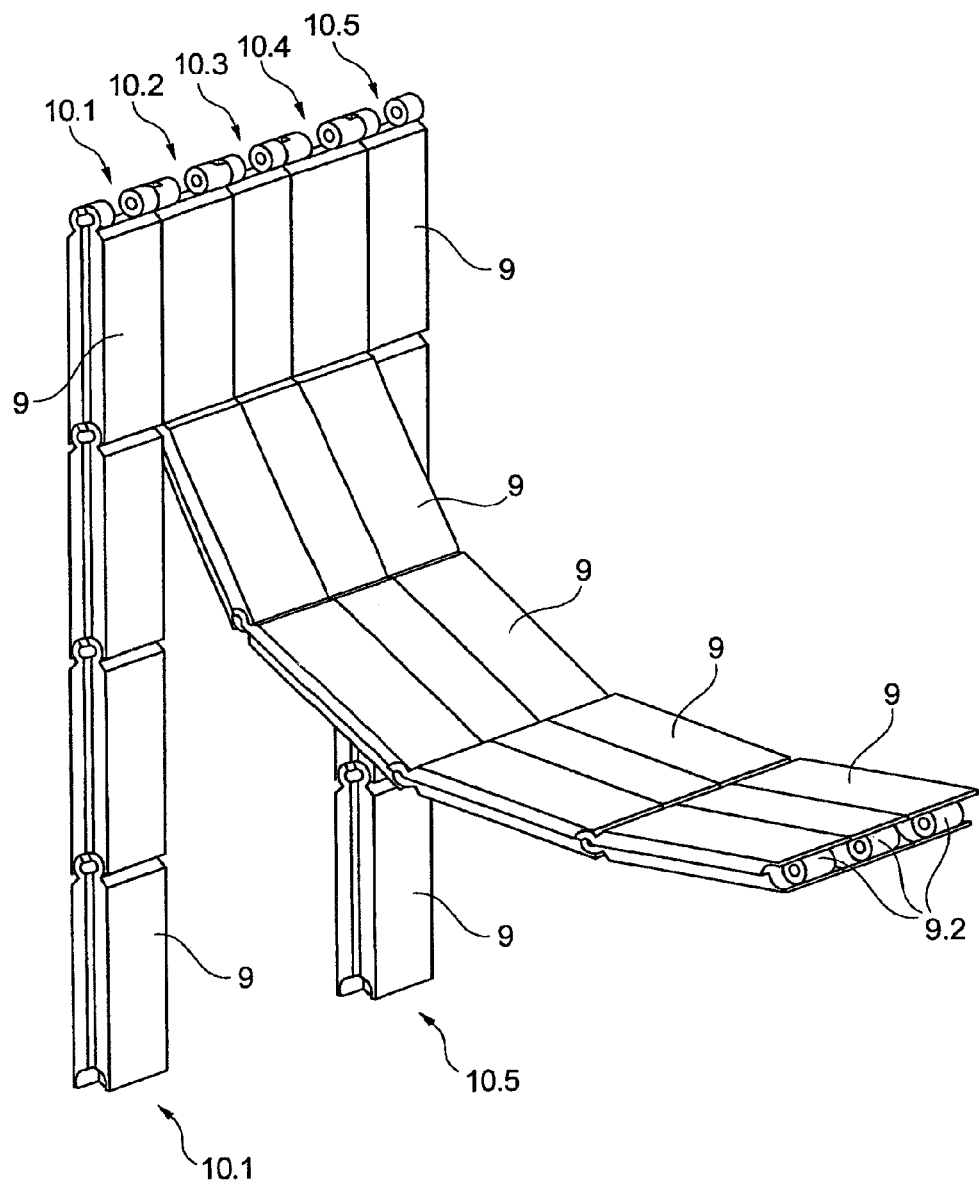
FIG. 6 shows the section of a curtain formed from a plurality of flat-top chains, whereby each chain has a plurality of plates as links.

At least one radiation protection curtain 8 each is disposed hanging downwardly at least at entrance 6 of radiation tunnel 2, preferably also at exit 7. If necessary, a plurality of radiation curtains can be arranged one behind the other at the entrance or exit of radiation tunnel 2. Radiation protection curtains 8 shield radiation tunnel 2 outwardly, so that no impermissible x-radiation escapes. The structure of a radiation protection curtain 8 is shown in greater detail in FIGS. 3 to 6:

Radiation protection curtain 8 is constructed of plates 9, which are connected together in the manner of a downwardly hanging flat-top chain 10.1-10.5 and are made of an x-ray-absorbing plastic composite, as is shown in FIG. 6.

Each plate 9 has at its upper and lower end in each case hinge elements 9.1, 9.2, which make it possible to connect two plates 9 hingedly. Preferably, hinge elements 9.1, 9.2 are configured as loops, and two plates 9 are connected together by insertion of a connecting pin in the loops. On one side, two loop-shaped elements 9.1 are disposed spaced apart. A central loop 9.2 is located on the opposite side. Central loop 9.2 can be moved between the two loops 9.1 of another plate 9 to create a connection. A long side of each plate 9 is made as a slightly protruding edge 9.3. Edge 9.3 makes it possible to arrange two plates 9 next to one another and with overlapping edges 9.3, so that no gap forms between two plates 9 of two neighboring chains 10.1-10.5, through which radiation could escape.

The protruding edge 9.3 is lengthened in the direction of hinge part 9.1 and thus serves as a stop, which limits the pivoting movement of two plates 9 relative to one another.

Each plate 9 preferably has smooth outer surfaces, so that friction in regard to an object 1 is reduced.

The width of a plate 9 and thereby the width of a chain 10.1-10.5 is preferably 10 mm-90 mm, preferably 15 mm-40 mm; in the example it is about 20 mm. The height of a plate 9, measured in the vertical direction of curtain 8 and in the longitudinal direction of a chain 10.1-10.5, is preferably between 20 mm and 60 mm, preferably 30 mm-50 mm, in the example about 40 mm. If the width of the opening of a radiation tunnel is 100 cm and the height of the opening 80 cm, radiation protection curtain 8 has at least 12 flat-top chains 10.1-10.5 hanging downwardly next to one another, whereby each flat-top chain 10.1-10.5 is constructed of at least 14 plates 9 as chain links.

Radiation curtain 8 completely closes the opening of the radiation tunnel above belt conveyor 3. To this end, each of its chains 10.1-10.5 is hung hingedly above the opening on the housing of radiation tunnel 8 and extends to belt conveyor 3. Curtain 8 is thereby hung so that its chains 10.1-10.5 can each pivot in the transport direction of belt conveyor 3. At the entrance side, therefore, they pivot inwardly into radiation tunnel 2, and outwardly at the exit side. An entering object 1, for example, an item of luggage, here presses plates 9 coming into contact with it forward, as a result of which said plates lie on the top side of the luggage and thus shield the radiation there as well. In the transverse direction, the curtain is opened only in the area of plates 9, which are in the conveying path of object 1 and are moved forward by said object.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A radiation protection curtain comprising a plurality of plates that are connectable to one another in a manner of a downwardly hanging flat-top chain and are made of an x-ray-absorbing plastic composite,
   wherein each of the plurality of plates has a top edge, a bottom edge and two side edges, the top edge and the bottom edge of each of the plurality of plates provided with at least one loop-shaped hinge element,
   wherein a bottom edge of a first plate is hingedly connected to a top edge of an adjacent second plate, such the second plate is positioned vertically below the first plate in the chain, and
   wherein one of the two side edges of each of the plurality of plates has a protruding edge, which facilitates the arrangement of two plates next to one another so as to provide overlapping edges.

2. The radiation protection curtain according to claim 1, wherein a width of a plate is 10 mm to 90 mm, 15 mm to 40 mm, or about 20 mm.

3. The radiation protection curtain according to claim 1, wherein a height of a plate is between 20 mm and 60 mm, between 30 mm to 50 mm, or about 40 mm.

4. The radiation protection curtain according to claim 1, wherein the plates have smooth outer surfaces.

5. The radiation protection curtain according to claim 1,
   wherein the top edge of the second plate has two spaced apart loop-shaped hinge elements and the bottom edge of the first plate has a single, centrally located loop-shaped hinge element, such that when the first plate is hingedly connected to the second plate, the single, centrally located loop-shaped element of the first plate is positioned between and aligned with the two spaced apart loop-shaped hinge elements of the second plate, and
   further comprising a pin that is slid through each of the aligned loop-shaped hinge elements to connect the loop-shaped hinge elements together.

6. The radiation protection curtain according to claim 1, wherein the bottom edge of the first plate is hingedly connected directly to the top edge of the adjacent second plate.

7. An x-ray inspection device for the examination of objects, particularly items of luggage, the device comprising:
   a radiation tunnel through which a conveying device for the objects is configured to run, the radiation tunnel having an entrance and an exit;
   a radiation source arranged in the radiation tunnel; and
   a radiation protection curtain arranged at the entrance and/or the exit of the radiation tunnel such that radiation in the radiation tunnel is shielded outwardly by the radiation protection curtain, the radiation protection curtain comprising a plurality of plates that are connectable to one another in a manner of a downwardly hanging flat-top chain and are made of an x-ray-absorbing plastic composite,
   wherein each of the plurality of plates has a top edge, a bottom edge and two side edges, the top edge and the bottom edge of each of the plurality of plates provided with at least one loop-shaped hinge element,
   wherein a bottom edge of a first plate is hingedly connected to a top edge of an adjacent second plate, such the second plate is positioned vertically below the first plate in the chain, and
   wherein the top edge of the second plate has two spaced apart loop-shaped hinge elements and the bottom edge of the first plate has a single, centrally located loop-shaped hinge element, such that when the first plate is hingedly connected to the second plate, the single, centrally located loop-shaped element of the first plate is positioned between and aligned with the two spaced apart loop-shaped hinge elements of the second plate, and
   further comprising a pin that is slid through each of the aligned loop-shaped hinge elements to connect the loop-shaped hinge elements together.

8. The x-ray inspection device according to claim 7, wherein the bottom edge of the first plate is hingedly connected directly to the top edge of the adjacent second plate.

9. A radiation protection curtain comprising:
a plurality of vertically hanging chains, each chain comprised of a plurality of plates connected adjacent to one another in a vertical direction,
wherein each of the plurality of plates are made of an x-ray-absorbing plastic composite,
wherein each of the plurality of plates has a top edge, a bottom edge and two side edges, the top edge and the bottom edge of each of the plurality of plates provided with at least one loop-shaped hinge element,
wherein a bottom edge of a first plate is hingedly connected to a top edge of an adjacent second plate, such the second plate is positioned vertically below the first plate, and
wherein the top edge of the second plate has two spaced apart loop-shaped hinge elements and the bottom edge of the first plate has a single, centrally located loop-shaped hinge element, such that when the first plate is hingedly connected to the second plate, the single, centrally located loop-shaped element of the first plate is positioned between and aligned with the two spaced apart loop-shaped hinge elements of the second plate, and
further comprising a pin that is slid through each of the aligned lop hinge elements to connect the loop-shaped hinge elements together.

10. The radiation protection curtain according to claim 9, wherein the bottom edge of the first plate is hingedly connected directly to the top edge of the adjacent second plate.

\* \* \* \* \*